(12) United States Patent
Schnee

(10) Patent No.: US 10,054,543 B2
(45) Date of Patent: Aug. 21, 2018

(54) MULTI-DIMENSIONAL CROSS-REACTIVE ARRAY FOR CHEMICAL SENSING

(71) Applicant: The United States of America, as represented by the Secretary of the Army, Washington, DC (US)

(72) Inventor: Vincent P. Schnee, Alexandria, VA (US)

(73) Assignee: THE UNITED STATES OF AMERICA, AS REPRESENTED BY THE SECRETARY OF THE ARMY, Washington, DC (US)

( * ) Notice: Subject to any disclaimer, the term of this patent is extended or adjusted under 35 U.S.C. 154(b) by 26 days.

(21) Appl. No.: 15/050,491

(22) Filed: Feb. 23, 2016

(65) Prior Publication Data

US 2017/0241910 A1    Aug. 24, 2017

(51) Int. Cl.
| | |
|---|---|
| *G01L 21/00* | (2006.01) |
| *G01N 21/64* | (2006.01) |
| *B82Y 15/00* | (2011.01) |

(52) U.S. Cl.
CPC ............ *G01N 21/643* (2013.01); *B82Y 15/00* (2013.01); *G01N 2201/062* (2013.01); *G01N 2201/12* (2013.01); *Y10S 977/954* (2013.01)

(58) Field of Classification Search
CPC .................. G01N 21/6454; G01N 21/6428
USPC ............................................. 422/82.08, 82.05
See application file for complete search history.

(56) References Cited

U.S. PATENT DOCUMENTS

| | | | |
|---|---|---|---|
| 5,338,659 A | 8/1994 | Kauvar et al. | |
| 5,605,612 A * | 2/1997 | Park ...................... | G01N 27/12 |
| | | | 204/429 |
| 7,189,353 B2 | 3/2007 | Lewis et al. | |
| 7,250,267 B2 | 7/2007 | Walt et al. | |
| 7,595,023 B2 | 9/2009 | Lewis et al. | |
| 8,778,690 B2 | 7/2014 | Sailor et al. | |
| 2003/0178607 A1* | 9/2003 | Swager .................. | B82Y 10/00 |
| | | | 252/582 |

OTHER PUBLICATIONS

Anzenbacher, Jr., P., Lubal, P., Buček, P., Palacios, M. A. & Kozelkova, M. E. A practical approach to optical cross-reactive sensor arrays. Chem. Soc. Rev. 39, 3954 (2010).
Albert, K. J. et al. Cross-Reactive Chemical Sensor Arrays. Chem. Rev. 100, 2595-2626 (2000.

* cited by examiner

*Primary Examiner* — Natalia Levkovich
(74) *Attorney, Agent, or Firm* — Richard J. Kim

(57) ABSTRACT

The discrimination ability of a chemical sensing cross-reactive arrays is enhanced by constructing sensing elements in two dimensions, first in the x-y plane of the substrate, second in the z dimension so that the sensors are vertically stacked on top of one another. Stacking sensing elements on top of one another adds to the discrimination ability by enabling the characteristic measurement of how fast target chemicals are passing through the stack of sensors. The new invention also allows the ability to discriminate components in a sample mixture by separating them using their innate difference in diffusional rates. Multi-sensor response patterns at each z level of sensors and time delay information from the sample passing from one level to the next are used to generate the response vector. The response vector is used to identify individual component samples and components in a mixture sample.

8 Claims, 6 Drawing Sheets

MULTI-DIMENSIONAL CROSS-REACTIVE ARRAY FOR CHEMICAL SENSING

GOVERNMENT INTEREST

The invention described herein may be manufactured, used, sold, imported, and/or licensed by or for the Government of the United States of America.

FIELD OF THE INVENTION

This invention relates in general to cross-reactive arrays for chemical sensing, and more particularly to multi-dimensional cross-reactive arrays for sensing explosive threats, chemical warfare agents, and toxic industrial chemicals.

BACKGROUND OF THE INVENTION

A cross-reactive array sensor is a device that mimics the sense of smell in mammals. It is generally thought that mammal's sense of smell, which is called olfaction, operates by the brain interpreting a complex patterned response from the olfactory bulb where odors interact with between 800-1200 different receptors. Each receptor in the olfactory bulb is slightly different so that when they all interact with the same odor they all respond slightly different making a pattern that is characteristic of that odor. Due the different chemical nature of each odor the olfactory bulb makes a unique pattern for each odor that is able to be distinguished.

Cross-reactive arrays mimic the sense of smell by using more than one broadly responsive (non-specific) chemical sensor to generate a patterned response which is then interpreted by a computer algorithm to identify the chemical being interrogated. These have been made using many different sensing methods including tin oxide sensors, carbon black polymer composites, fluorescent polymers, carbon nanotubes, inorganic dyes, quantum dots, functionalized metallic nanoparticles, and others. A few good references on these type of devices are, e.g., Anzenbacher, Jr., P., Lubal, P., Buček, P., Palacios, M. A. & Kozelkova, M. E. A practical approach to optical cross-reactive sensor arrays. Chem. Soc. Rev. 39, 3954 (2010); and Albert, K. J. et al. Cross-Reactive Chemical Sensor Arrays. Chem. Rev. 100, 2595-2626 (2000).

All of the previous examples of cross-reactive arrays placed the sensing elements on the same plane where they interact with the sample. Additionally, all cross-reactive arrays are poor at identifying components in a mixture sample. This invention is similar but different than U.S. Pat. No. 7,189,353 B2. U.S. Pat. No. 7,189,353, entitled, "Use of spatiotemporal response behavior in sensor arrays to detect analytes in fluids," discloses a time delay feature added to the feature vector for added discrimination ability and components in a mixture can theoretically be discriminated.

Other references worth mentioning are Cross-reactive sensors, U.S. Pat. No. 7,250,267 B2 issued to Walt et al.; and Method for determining analyte concentration by cross-reactivity profiling, U.S. Pat. No. 5,338,659 A issued to Kauvar et al.

SUMMARY OF THE INVENTION

The disclosure relates to fabricating a chemical sensor that can be used by the Army to sense explosive threats, chemical warfare agents, and toxic industrial chemicals. It may be used by the food and beverage industries in quality control relating to spoilage, ripeness, and uniformity of a manufactured item. The disclosure may also find relevance in medical uses as a diagnostic tool for detecting disease.

Other devices of this type are referred to as cross-reactive arrays, electronic noses, and multiplexed sensors. Cross-reactive arrays are disclosed with out-of-plane stacking of sensors to generate time-dependent responses, which are then combined with different z-level array descriptors. Additionally, diffusion of volatile chemicals through solid medium is much slower than through gas or liquid, making an effective device for identifying mixture samples much smaller. The device is smaller because a slower diffusion rate makes the distance needed to separate components in a mixture much shorter.

Methods of making artificial olfactory systems rely on non-specific sensors which respond in concert generating a pattern that can be identified as the odorant impinging upon the sensor. The response pattern is formed by using chemically different sensors whose response to a single analyte is varied. The difference of the sensors on the molecular level generates the varying changes in the transduction, and features such as total magnitude of response, percent change of response, and amount of spectral change are used to make the descriptive pattern response.

This invention adds more descriptive information to the response pattern by arranging the elements of a cross-reactive array in a 2 dimensional manner, the first dimension is the direction of the sample flow in the sensor so that the sample interacts with each sensor in a sequential manner through the gas or liquid sample carrier medium. The first dimension is in the x and y plane of the substrate that the device is constructed on. The stacking of the sensors happens in the z dimension of the substrate. The sensors are stacked in intimate contact one on top of another so that the only way for a sample to interact with underlying sensors it to pass through the sensor on top of it. The stacking of the sensors adds a time dependent response to the underlying sensors based upon the diffusion the sample through the sensor layers. The diffusion time of the samples through the sensor is based upon the thickness of the sensor layers, density of the sensor layer, and chemical interactions that take place. The information added to the response pattern is the diffusion constants, and difference in time it takes for each sensor to respond. The diffusion constant and time delay are two characteristic features that can be added to the response pattern for discrimination.

This type of device can be constructed with any of the previously reported sensor types that are permeable to volatile chemicals.

BRIEF DESCRIPTION OF THE DRAWINGS

Additional advantages and features will become apparent as the subject invention becomes better understood by reference to the following detailed description when considered in conjunction with the accompanying drawings wherein.

DETAILED DESCRIPTION

Methods of making artificial olfactory systems (cross-reactive arrays) rely on non-specific sensors which respond in concert generating a pattern that can be identified as the odorant impinging upon the sensor. The response pattern is formed by using chemically different sensors who response to a single analyte is varied. The difference of the sensors on the molecular level generates the varying changes in the transduction and features such as total magnitude of response, percent change of response, fitting of polynomial lines, and amount of spectral change are used to make the descriptive response patterns.

Figure 1:
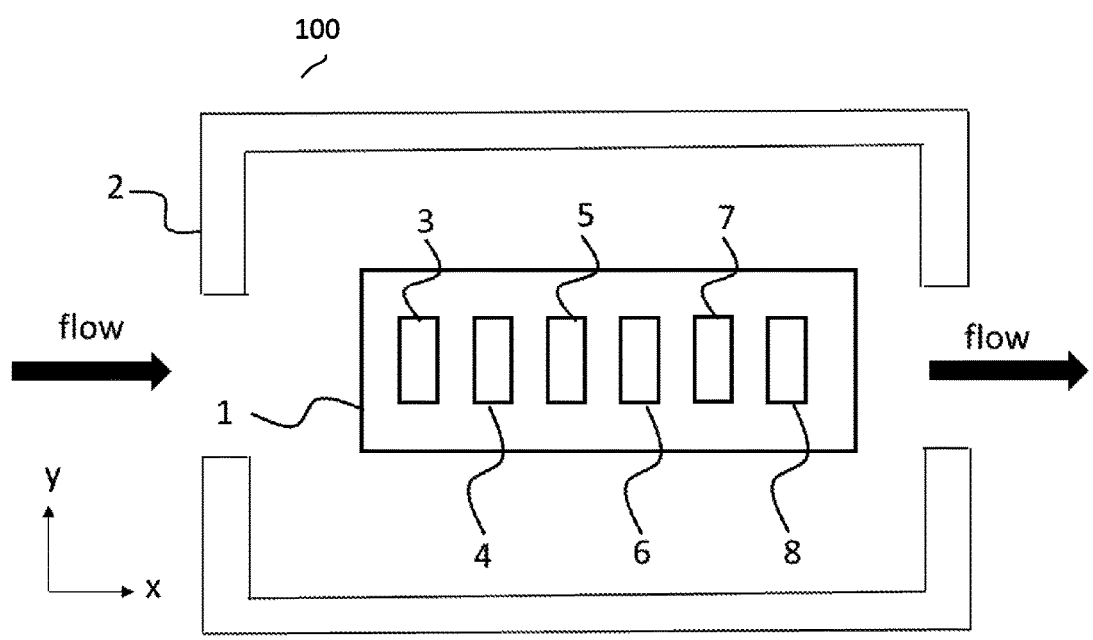
FIG. 1 shows an exemplary 2-dimensional cross-reactive array having a sensor substrate in an enclosure.
Figure 2:
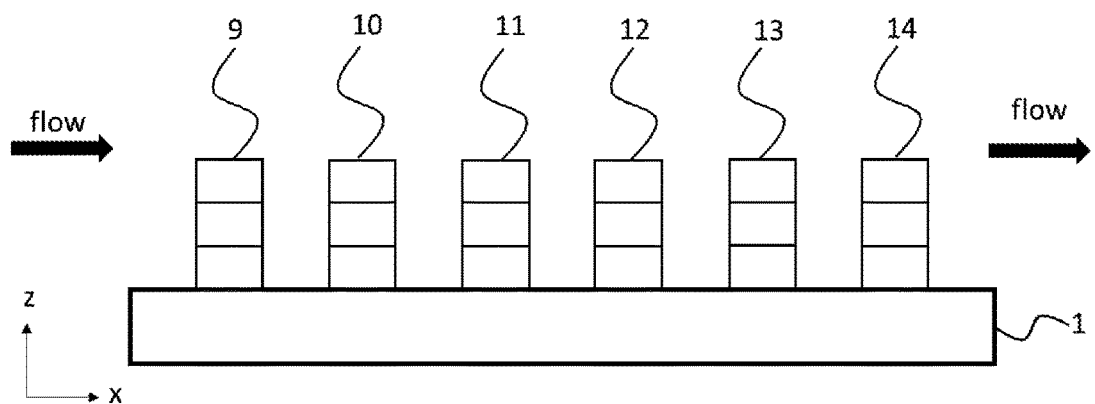
FIG. 2 shows an exemplary z-dimensional stacking of sensor elements.
Figure 3:
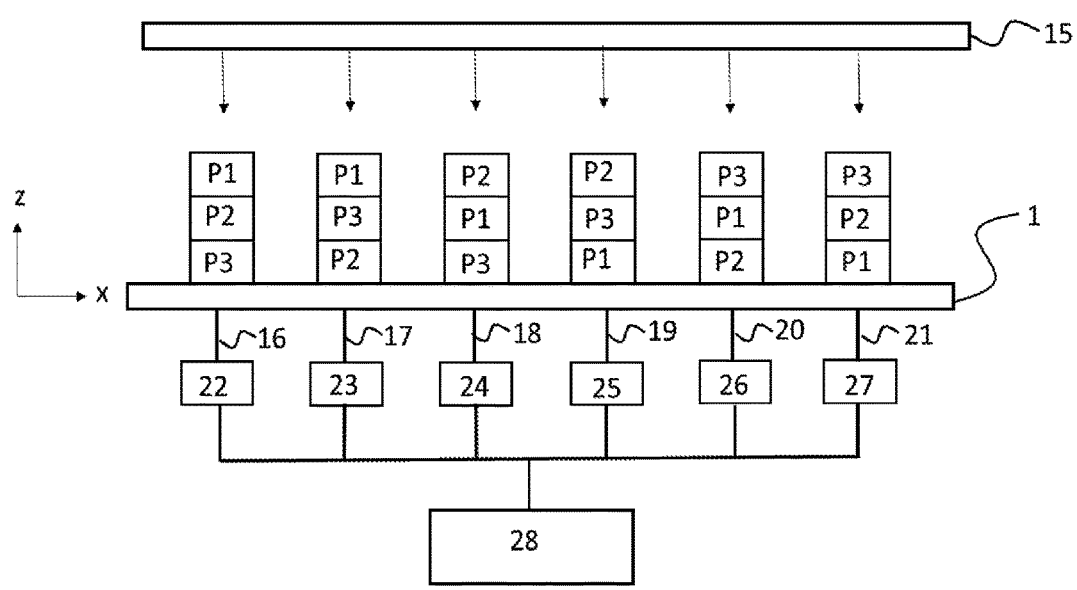
FIG. 3 shows a schematic of an exemplary three polymer system excitation using a light source such as a 365 nm LED.
Figure 4:
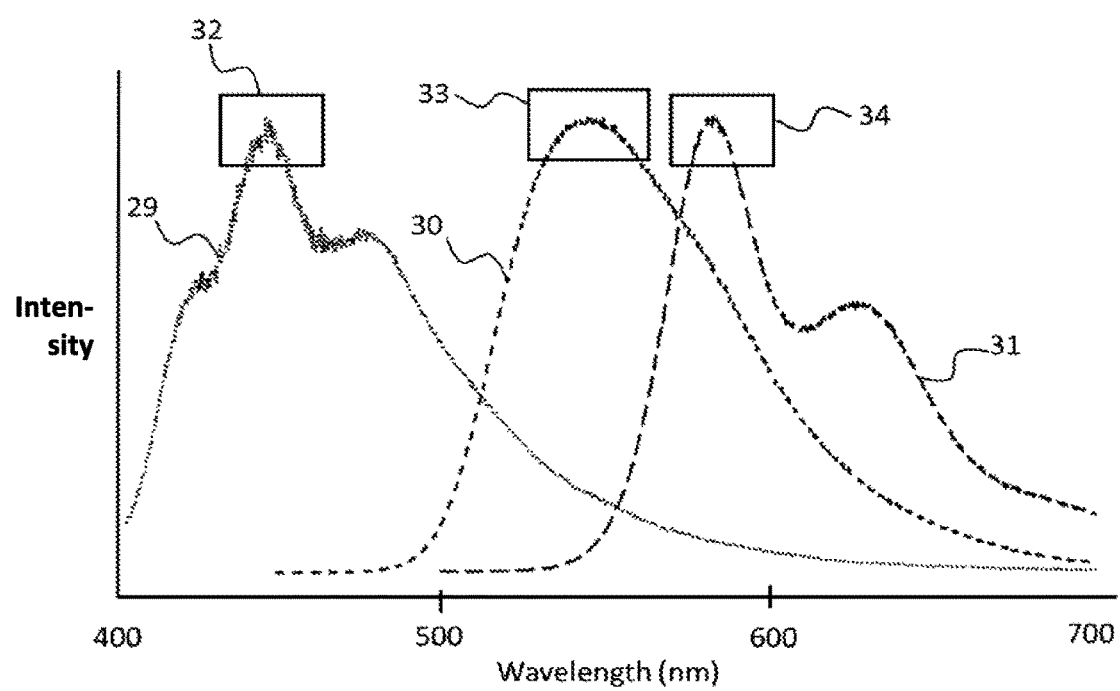
FIG. 4 shows exemplary spectral bands of three fluorescent polymer system.

This invention adds more descriptive information to the response pattern by arranging the elements of a cross-reactive array in a 2 dimensional manner, the first dimension is the direction of the sample flow in the sensor so that the sample interacts with each sensor in a sequential manner through the gas or liquid sample carrier medium. This is shown in FIG. 1 where 1 the sensor substrate which can be quartz for optical based sensors or silicon for electrical based sensors is in an enclosure 2. The areas where the stacks of sensor elements are laid out so that the flow interacts with them sequentially in the flow path are show as elements 3-8. The first dimension is in the x and y plane of the substrate that the device is constructed on. The stacking of the sensors happens in the z-dimension of the substrate shown in FIG. 2 where elements 9-14 are stacks of sensing elements. In this exemplary embodiment, the sensors are stacked in intimate contact one on top of another so that the only way for a sample to interact with underlying sensors is to pass through the sensor on top of it. The stacking of the sensors adds a time dependent response to the underlying sensors based upon diffusion of the sample through the upper sensor layers. The sensors in each z-stack have to be responsive to the same classes of chemicals so that the passage of a chemical from one layer to the next can be measured. Each sensor in the z-stacked also needs to be individually addressable so each one can be monitored for changes over time. A way to make a stack of individually addressable stacked sensors is to use fluorescent polymers whose emission intensity is dependent on their local environment. Each of the fluorescent polymers in the z-stack have to have emission spectrums that are spectrally separated enough to monitor each emission peak with a spectrometer. An example of this type of fluorescent polymer z-stack are these three polymers; Poly[2,5-bisoctyloxy)-1,4-phenylenevinylene] (P1) with a emission between 540-560 nm, Poly(9,9-dioctylfluorene-alt-benzothiadiazole) (P2) with emission between 515-535 nm and Poly[(9,9-dihexyl-fluoren-2,7-diyl)-co-(anthracen-9,10-diyl)] (P3) with emission between 450-435 nm. This three polymer system is also excitable with a common light source such as a 365 nm LED. A schematic of this device is in FIG. 3, where 15 is an excitation light source such as a 365 nm LED. The light source 15 is focused onto the polymers P1-P3 causing them to emit fluorescence which is collected by an optical system such as a fiber optic cable seen as elements 16-21 which passes the emitted light from each stack of sensors to a separate spectrometer elements 22-27. All of the spectrometers are connected to a computer element 28 which is used to select wavelength bands from each spectrometer output characteristic of each fluorescent polymer in the sensor stacks for each stack throughout the array. The spectrums measured by each spectrometer and the selected spectral bands of this three fluorescent polymer system are shown in FIG. 4. Where elements 29-31 are the fluorescence emission spectrums of P1-P3 respectively. The bands which are monitored to characterize the different fluorescent polymers are indicate in elements 32-34. In addition to these polymers being individually addressable with a spectrometer they are so structurally different enough to provide a robust cross-reactive array response.

A second method of making a z-stack of fluorescent sensors is to use a fluorescent nanocrystal/polymer composite. Fluorescence emission from nanocrystals is a size dependent property with narrow emission spectrums. The nanocrystals narrow emission spectrums allow more sensors to be stacked in the z-direction and still be able to be spectrally resolved using a spectrometer. A z-stack sensor array can be constructed using a set of CdSe nanocrystals of sizes 2.2, 2.5 3.3, 4.5 nm with emission maxima of 480, 520, 560, 600 nm respectively in the same manner as FIGS. 3 and 4. This set of nanocrystal can then be mixed with any non-fluorescent polymer to add chemical diversity such as this set, Poly(vinyl stearate), Poly(benzyl methacrylate), Poly(methyl methacrylate), Poly(ethylene-co-vinyl acetate). Each stack of sensors in must only contain one composite of each size nanocrystal so that different layers of the stack can be monitored independently.

A third way of making individually addressable sensor is to use a stack of chemiresistors with insulating buffer layer in between them. An example of chemiresistor chemical sensor suitable for z-stacking include modified carbon nanotubes, carbon nanotube polymer composites, and polymer carbon black composites.

Figure 5:
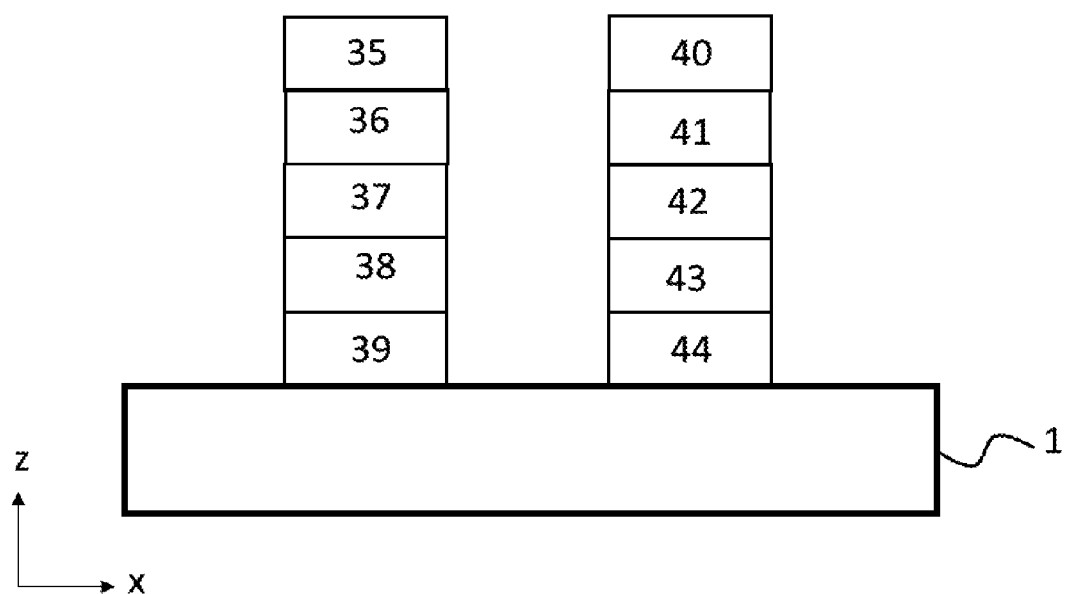
FIG. 5 shows exemplary z-stacked sensors in which a non-responsive permeable buffer layer is added in between sensor layers.

In all iterations of z-stacked sensors a non-responsive permeable buffer layer can be added in between the sensor layer to increase the migration time between sensors as seen in FIG. 5. Where elements 35, 37, 39, 40, 42, and 44 are sensors and elements 36, 38, 41, and 43 are permeable buffer layers. The buffer layers increase the resolution of multi-analyte samples by increasing the time selective differential partitioning happens between sensors. Buffer layers can include neat forms of the polymers used in the sensing composites or other types of polymers such as siloxanes used in gas chromatography. The diffusion time of the samples through the sensor is based upon the thickness of the sensor layers, density of the sensor layer, chemical interactions that take place, and the time added for the sample to pass through the buffer layer.

Figure 6A:
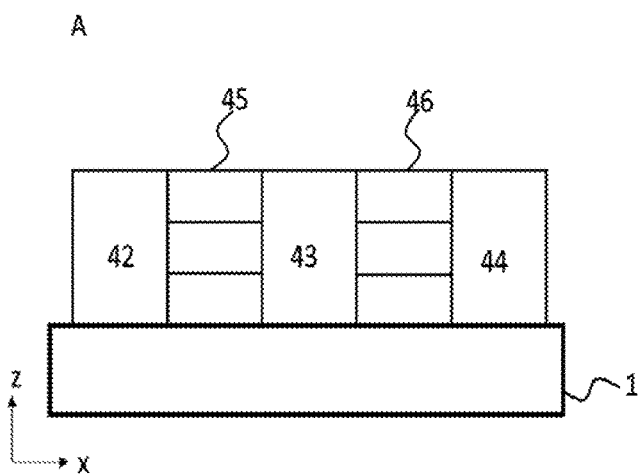
FIG. 6*a* shows exemplary stacked sensor layers spaced in the x and y direction by impermeable blocking layers.
Figure 6B:
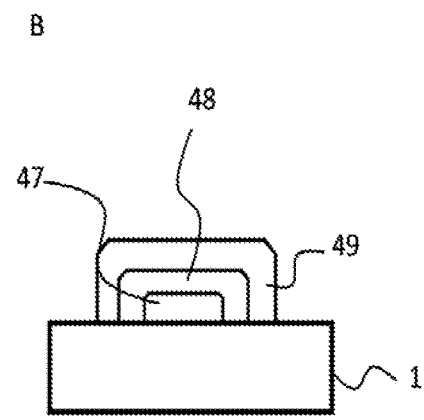
FIG. 6*b* shows an alternate stacking sensor layering in which successive sensor layer each completely covers the sensor layer below.

There are several methods for constructing an array of z-stacked sensors including, stamping, thermal evaporation, and inkjet printing. Stamping of the fluorescent polymer and polymer composite materials is done with a polydimethlsiloxane made with Dow Corning Sylgard 184 with is cast onto a template of the desired sensor size and allowed to cure. The cured stamp then has the fluorescent polymer or polymer composite spun cast onto it from a solvent. The solvent is evaporated from the stamp leaving a layer of the sensing material. The inked stamp is then placed sensor side down on the sensor substrate and heated above the glass transition temperature of the polymer. The stamp is then removed from the substrate leaving behind the sensor layer. This stamping process is repeated with different sensing layers in the same location on the substrate to form the z-stacked sensor array. Stamping can also be used to create the buffer layers between the sensor layers. It is ideal to have the sample chemicals enter the z-stack from the top of the stack and not from the side walls of the stack. To prevent unwanted intrusion in the sensor stack two methods can be used with stamping. First, is to stamp sensor layers between an impermeable blocking layers that are defined by photo-lithograph which are impermeable to the chemicals that are being sensed. The second method is to construct the layers in a manner where the over coating layers are larger in size and fully cover the underlying layers eliminating any side-walls. These two methods are seen in FIGS. 6a and 6b, where in FIG. 6a, 45 and 46 are stacked sensor layers and in intimate contact with them in the x and y direction are elements 42-44 which are impermeable blocking layers. In FIG. 6b the closest sensor layer to the substrate 47 is then completely covered by the next sensor layer 48 which is then completely covered the next sensor layer 49 until the desired number of sensor layer is achieved.

Thermal evaporation of sensing layer can be achieved by multiple depositions of the sensing material on top of one another. The positions of the sensing material is defined by shadow masking the sensor substrate.

Inkjet printing can also create stacked sensor layer structures by using an immiscible solvent system with a buffer layer between sensors. This process involves printing the first layer such as a fluorescent polymer in an organic solvent like Chloroform. The next layer deposited would then need to be in a solvent that will not perturb the underlying layer such as a water solution of poly(diallydimethylammonium chloride). This process of immiscible solvent layers is then repeated until the desired number of sensor layer is achieved.

This system operates with a flow path of gas or liquid above the array of stacked sensors. Into that flow path pulses of samples are introduced to interact with the sensor. The sensors at each z level are monitored in the same manner as traditional cross-reactive arrays where each sensor's response in the array is analyzed, selecting characteristic features from it. The features from each sensor are then aggregated to create a feature vector. The feature vector is then compared to known feature vectors to make sample identification. This invention by stacking sensor elements adds new information to the feature vector that was previously not measureable. The new information is difference in time from when vertically adjacent sensors start to respond. This time is characteristic of how long it took of the analyte to pass through the top sensor. The information added to the response pattern is the diffusion constants, and difference in time it takes for each sensor to respond. The diffusion constant and time delay are two characteristic features that can be added to the response pattern for discrimination. The addition of non-responsive buffer layer between the sensor layers allows for tuning the time differential for chemicals passing through the stack of sensors improving the array discriminating ability. Also increasing the resolving power for multicomponent samples.

It is obvious that many modifications and variations of the present invention are possible in light of the above teachings. It is therefore to be understood that within the scope of the appended claims, the invention may be practiced otherwise than as described.

What is claimed is:

1. An enclosed cross-reactive array for chemical sensing, comprising:
    a cross-reactive array, comprising
        a flat sensor substrate having an upper surface of stack areas, and
        stacks of fluorescent chemical sensing polymer layers disposed on the upper surface of the sensor substrate, wherein the fluorescent chemical sensing polymer layers of a given stack are sequentially stacked such that each stack of fluorescent chemical sensing polymer layers rises from a respective stack area as a unique sequence of fluorescent chemical sensing polymer layers perpendicular to the surface of the flat sensor substrate, each stack resulting in a uniquely sequenced stack of fluorescent chemical sensing polymer layers having a respectively exposed upper sensor layer, each fluorescent chemical sensing polymer layer being respectively chosen from a group of fluorescent chemical sensing polymers consisting of Poly[2,5-bisoctyloxy)-1,4-phenylenevinylene], Poly(9,9-dioctylfluorene-alt-benzothiadiazole), and Poly[(9,9-dihexylfluoren-2,7-diyl)-co-(anthracen-9,10-diyl)], each fluorescent chemical sensing polymer in the group characterized by a unique fluorescent emission spectrum having a distinct emission peak; and
    an enclosure enclosing the cross-reactive array, but having open ends such that a carrier medium carries a chemical sample across the sequentially laid out stack areas on the surface of the flat sensor substrate from one open end to another open end of the enclosure.

2. The multi-dimensional cross-reactive array as recited in claim 1, wherein said flat sensor substrate is comprised of quartz for optical based sensors or silicon for electrical based sensors.

3. The multi-dimensional cross-reactive array as recited in claim 1, wherein said carrier medium is either a gas or liquid sample carrier medium.

4. The multi-dimensional cross-reactive array as recited in claim 1, comprising a non-responsive permeable buffer layer disposed between the fluorescent chemical sensing polymer layers to increase a migration time between sensors.

5. The multi-dimensional cross-reactive array as recited in claim 1, wherein the fluorescent chemical sensing polymer layers are stacked by stamping of fluorescent polymer materials.

6. The multi-dimensional cross-reactive array as recited in claim 1, wherein the fluorescent chemical sensing polymer layers are stacked by inkjet printing of fluorescent chemical sensing polymer layers with a buffer layer between stacked fluorescent chemical sensing polymer layers.

7. A chemical sensing device based on an enclosed cross-reactive array according to claim 1, comprising:
    the cross-reactive array of claim 1;
    a light source focused onto the multi-dimensional cross-reactive array to cause each of the stacked fluorescent chemical sensing polymer layers to emit a respective fluorescence;
    an optical system based on fiber optic cables for passing the respectively emitted light from each stack of fluorescent chemical sensing polymer layers to a respective spectrometer elements to produce a respective spectrometer output; and
    a computing device connected to receive and process each spectrometer output for select wavelength bands to characterize each fluorescent chemical sensing polymer layer in the stack associated with the respective spectrometer output throughout the array.

8. The chemical sensing device as recited in claim 7, wherein the light source is comprised of a 365 nm LED.

* * * * *